(12) United States Patent
Olsson et al.

(10) Patent No.: US 8,205,611 B2
(45) Date of Patent: *Jun. 26, 2012

(54) DRY POWDER INHALER

(75) Inventors: Magnus Olsson, Lund (SE); Eva Trofast, Lund (SE)

(73) Assignee: AstraZeneca AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/876,493

(22) Filed: Sep. 7, 2010

(65) Prior Publication Data

US 2011/0056089 A1 Mar. 10, 2011

Related U.S. Application Data

(63) Continuation of application No. 10/574,873, filed as application No. PCT/GB2004/004202 on Oct. 4, 2004, now Pat. No. 7,896,005.

(30) Foreign Application Priority Data

Oct. 7, 2003 (SE) ........................................ 0302665

(51) Int. Cl.
*A61M 11/00* (2006.01)

(52) U.S. Cl. .......... 128/203.12; 128/200.23; 128/200.24

(58) Field of Classification Search ............. 128/203.12, 128/204.18, 200.14, 200.23, 200.24
See application file for complete search history.

(56) References Cited

U.S. PATENT DOCUMENTS

| 4,524,769 A * | 6/1985 | Wetterlin ................. 128/203.15 |
| 6,390,291 B1 * | 5/2002 | Garrill et al. ................... 206/204 |
| 2002/0048552 A1 * | 4/2002 | Garrill et al. ..................... 424/45 |

\* cited by examiner

*Primary Examiner* — Steven Douglas
(74) *Attorney, Agent, or Firm* — Finnegan, Henderson, Farabow, Garrett & Dunner, L.L.P.

(57) ABSTRACT

A processing method and apparatus are disclosed for processing an inhaler component of a dry powder inhaler so as to remove any electrostatic charge and improve inhaler performance in drug delivery to the respiratory tract. The method includes exposing the inhaler component, while it contains an amount of medicament, to a gas in a chamber at a first predetermined pressure; exposing the inhaler component, in the chamber, to gas at a second pressure greater than the first pressure; and repeating the exposure of the inhaler component to gas at a pressure no greater than the first predetermined pressure.

31 Claims, 2 Drawing Sheets

Figure 1:
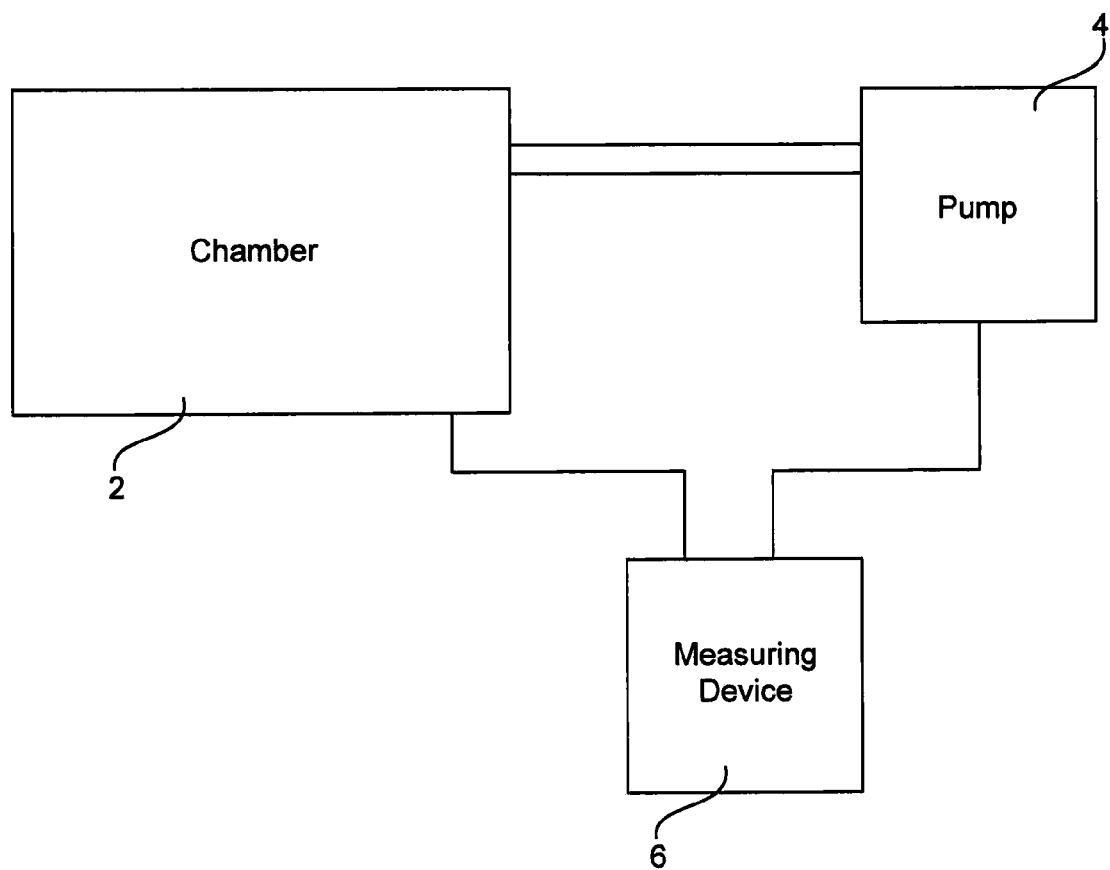

DRY POWDER INHALER

This is a continuation of application Ser. No. 10/574,873, filed Apr. 6, 2006 now U.S. Pat. No. 7,896,005, which is a national phase application under 35 U.S.C. §371 of PCT International Application No. PCT/GB2004/004202, filed Oct. 4, 2004, which claims priority to Swedish Application No. 0302665-5, filed Oct. 7, 2003, all of which are incorporated herein by reference in their entireties.

The present invention relates to a processing method and apparatus, more particularly, to processing a body so as to remove any electrostatic charge and improve inhaler performance in drug delivery to the respiratory tract. In the manufacture of many devices, there has been the problem that components of the device acquire electrostatic charges, which remain during assembly and/or sale. To overcome the problem, it has been proposed to use Corona dischargers, in particular by providing ions by using Corona ionisation. The irradiated ions are used to neutralise electrostatic charges on components of the devices.

The use of Corona discharges is itself problematic. In particular, the discharges are awkward to handle and need to be brought into close proximity with any device to be discharged. Even then, by virtue of the nature of a Corona discharger, the discharging ions are irradiated in a somewhat directional manner, such that it is difficult to ensure complete discharge of the innermost components of the device. It is also difficult to achieve uniform discharge of surfaces of the device. Indeed, surfaces near the Corona discharger may actually become charged by it.

The charge induced on the plastic inhaler device by the patient has not been extensively studied. It is speculated that a reduced bioavailability might result from a higher proportion of drug being retained in the inhaler from the more highly charged device and adhered to the carrier particles in the drug formulation.

It has been suggested that a pressure reduction induced discharge can be used as a surface charge elimination method (J. Electrostatic 49 (2000), 15-22), but nothing is said or implied of any influence of such treatment on improving the performance of a drug delivery device for inhalation. The performance of such a drug delivery device is depending on the complex interactions between the device and the drug formulation per se.

Dry powders tend to become electrostatically charged. Triboelectrification in pharmaceutical powders is a very complicated and ill-defined process although it has been shown to be influenced by many factors, such as particle size and shape, physicochemical properties of the contacting surface, contact area and frequency, surface purity and atmospheric conditions (Powder Technology, 37 (1), 71-85 (1984).

Electrostatic charging occurs during nearly every powder-handling process such as milling, micronisation, flow, fluidisation, tabletting and capsule filling.

Electrostatic charge can also arise from collisions between particles and the container walls. Triboelectrification is also one of the major reasons why powders stick to the walls of any contacting containers. This creates a problem for a plastic inhaler where it is desired to get an accurate and uniform dose every time.

Moisture sorption of the particle surface is one of the most effective ways to remove surface charge. This is contradictory to what is desired in dry powder inhalers.

The handling of micronised powder for use in dry powder inhalers may be due to particle agglomeration, cohesion and adhesion to manufacture equipment, inhaler devices and container materials. WO 02/80884 relates to a method for the surface modification of powders in order to reduce electrostatic chargeability of the fine particles thereby improving powder flow properties during the manufacture of the dry powder inhalers and improving powder dispensing properties during application. By surface modification of the active substance the electrostatic charge acquisition by triboelectrification during the pharmaceutical processing and during handling/drug administration has been reduced.

WO 03/35028 discloses modulation of charge density to produce improvements in the characteristics of spray-dried proteins.

We have now found that low pressure treatment of the part(s) of the dry powder inhaler, the empty dry powder inhaler, the inhaler filled with the powder formulation or the formulation per se will reduce the charges from the plastic details or the powder and give high performance characteristics of the inhaler i.e. dose uniformity.

In a first aspect the invention therefore provides a process for the preparation of a dry powder inhaler which comprises, during manufacture, exposing a dry powder inhaler optionally filled with a powder formulation, or one or more components thereof, to a gas at low pressure.

The process of the invention can be used during the complete manufacture of an inhaler or during the partial manufacture of an inhaler.

The gas is preferably air at a pressure of less than 200 mbar, preferably less than 100 mbar, more preferably less than 50 mbar and most preferably less than 1 mbar.

According to the present invention, there is also provided an apparatus for removing an electrostatic charge from a dry powder inhaler optionally filled with a powder formulation, or one or more components thereof, the apparatus comprising:
 i) a chamber for containing one or more inhaler components, or a complete inhaler, optionally filled with a powder formulation,
 ii) a device for reducing the pressure of gas in the chamber
 iii) a controller/device for a) reducing the pressure of gas in the chamber and b) then returning the pressure to atmospheric pressure The controller/device for step suitable reduces the pressure to a value sufficiently low that ions of the gas, which accelerate under the influence of the electrostatic field of the a dry powder inhaler or components thereof, travel sufficiently far between collisions and gain sufficient energy, upon collision, ionise another molecule and trigger an avalanche.

In a further aspect the invention provides a process for reducing electrostatic charges from a dry powder inhaler optionally filed with a powder formulation, or one or more components thereof, the process comprising:
 i) placing a dry powder inhaler optionally filled with a powder formulation, or one or more components thereof in a chamber,
 ii) reducing the pressure of gas in the chamber,
 iii) returning the pressure to atmospheric pressure
 iv) optionally repeating steps ii) and An advantage of the invention is that the process can be accomplished at ambient temperature.

According to the present invention, there is provided a method of removing an electrostatic charge from a dry powder inhaler optionally filled with a powder formulation, or one or more components thereof, the method comprising the step of exposing one or more inhaler components, or a complete inhaler, optionally filled with a powder formulation one or more times to a gas, preferably air, at a pressure of no more than 200 mbar, preferably less than 50 mbar and most preferably less than 1 mbar. In the case of powder present, the charges will be removed from the powder as well. Preferably the process of discharge is repeated a number of times. Optionally the powder could be treated alone.

The present invention will be more clearly understood from the following description, given by way of example only, with reference to the accompanying drawings.

FIG. 1 illustrates schematically an apparatus embodying the present invention. One or more assembled, or at least partly assembled inhalation devices are placed into a chamber 2 which, after being closed has its internal pressure reduced by a pump 4. A measuring device 6 is provided to control the pump 4 so as to reduce the air pressure in the chamber 2 to a desired perssure. The measuring device 6 is preferably configurated automatically to control the system to repeat the process a plurality of times. It is generally only necessary to fully decompress the chamber 2 two or three times in order to effectively remove substantially all electrostatic charges from the device and/or powder.

As a result, the internal working parts of the inhalation device may be kept free of electrostatic charges for subsequent sale and use of the device.

A plurality of devices may be put in the chamber at once. In particular, a container (not shown), such as a bag, holding the device may be put in the chamber 2 and, after decompression, closed for the transportation of the devices.

Figure 2:
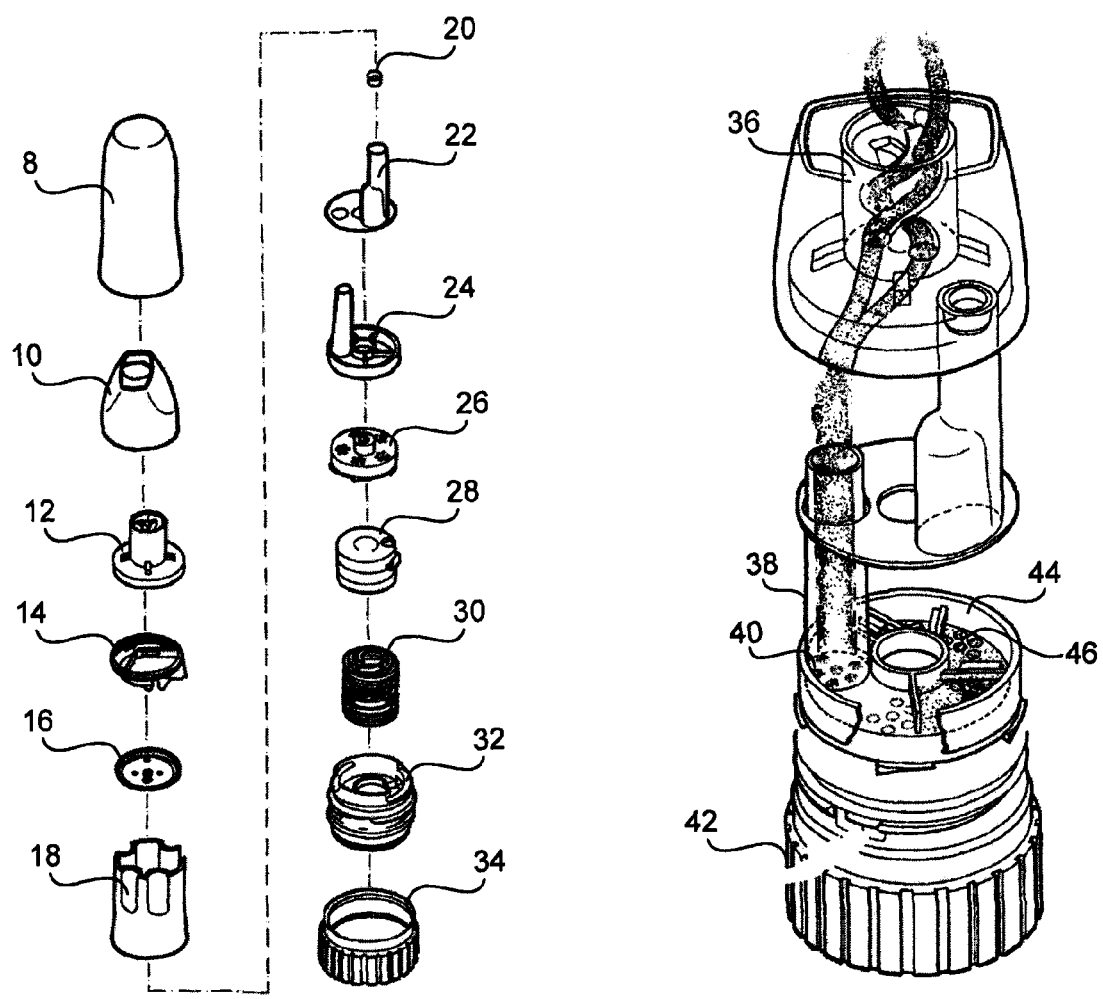

FIG. 2 illustrates component parts of an inhalation device which is for storing and dispensing predetermined doses of dry powder for inhalation. These parts are typically produced from one or more polymer materials and will almost certainly acquire electrostatic charges during the steps of injection moulding, handling and assembly. Thus, when assembled, the inhalation device will typically have a number of internal electrostatic charges, often of conflicting polarity in adjacent parts. Indeed, dry powder is almost always inevitably charged.

As will be appreciated, dry powder of a size suitable for inhalation is particularly sensitive to electrostatic forces. Therefore, for an inhalation device such as illustrated in FIG. 2, but not limited hereto, it is particularly desirable to reduce any electrostatic charges in the component parts of the device.

The effect of electrostatic discharge at low pressures for the performance of an inhalation device has not previously been recognised. The method of using low perssure has many technical and economical advantages compared to other possible methods of reducing charges e.g. ethanol treatment of plastic details (needs drying processes etc).

Medicaments suitable for administration by using the present invention are any which may be delivered by inhalation. Suitable inhalable medicaments include for example β2-adrenoceptor agonists for example salbutamol, terbutaline, rimiterol, fenoterol, reproterol, bitolterol, salmeterol, formoterol, clenbuterol, procaterol, broxaterol, picnmeterol, TA-2005 (chemically identified as 2(1H)-Quinolone, 8-hydroxy-5-[1-hydroxy-2-[[2-(4-methoxyphenyl)-1-methylethyl]amino]ethyl]-monohydrochloride, [R—R*,R*] also identified by Chemical Abstract Service Registry Number 137888-11-0 and disclosed in U.S. Pat. No. 4,579,854), mabuterol, formanilide derivatives like 3-(4-{[6-({(2R)-2-[3-formylamino)-4-hydroxyphenyl]-2-hydroxyethyl}amino)hexyl]oxy}butyl)benzensulfonamide as disclosed in WO 2002/76933 or as in U.S. Pat. No. 6,576,793, aryl aniline derivatives as in WO 2003/42164, benzensulfonamide derivatives like 3-(4-{[6-({(2R)-2-hydroxy-2-[4-hydroxy-3-(hydroxymethyl)phenyl]ethyl}amino)-hexyl]oxy}butyl)benzenesulfonamide as disclosed in WO 2002/88167, and the like; glucocorticosteroids such as budesonide, fluticasone (e.g. as propionate ester), mometasone (e.g. as furoate ester), beclomethasone (as 17-propionate or 17,21-dipropionate esters), ciclesonide, triamcinolone (e.g. as acetonide), flunisolide, zoticasone, flumoxonide, rofleponide, butixocort (e.g. as propionate ester), prednisolone, prednisone, tipredane, steroid esters according to WO 2002/12265, WO 2002/12266 and WO 2002/88167 (e.d. 6α,9α-difluoro-17α-[2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydrofuran-3S-yl) ester and 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester; anticholinergic bronchodilators such as tolterodine, ipratropium bromide, tiotropium bromide and oxitropium bromide; PDE-IV inhibitors; antihistamines; expectorants; mucolytics; cyclooxygenase inhibitors; leukotriene synthesis inhibitors; leukotriene antagonists; phospholipase-A2 inhibitors; platelet aggregating factor (PAF) antagonists and prophylactics of asthma and chronic obstructive pulmonary disease (COPD), antiarrhytmic medicaments, tranquilisers, statins, cardiac glycosides, hormones, antihypertensive medicaments, antidiabetic-, antiparasitic and anticancer medicaments, sedatives and analgesic medicaments, antibiotics, antirheumatic medicaments, immunotherapies, antifungal and antihypotension medicaments, vaccines, antiviral medicaments, proteins, polypeptides and peptides for example peptide hormones and growth factors, polypeptides vaccines, enzymes, endorphines, lipoproteins and polypeptides involved in the blood coagulation cascade, vitamines and others, for example cell surface receptor blockers, antioxidants and free radical scavengers.

Several of these compounds could be administered in the form of pharmacologically acceptable esters, acetals, salts, solvates, such as hydrates, or solvates of such esters or salts, if any. Both racemic mixtures as well as one or more optical isomers of the above compounds are within the scope of the invention.

Suitable physiologically acceptable salts include acid addition salts derived from inorganic and organic acids, for example the chloride, bromide, sulphate, phosphate, maleate, fumarate, citrate, tartrate, benzoate, 4-methoxybenzoate, 2- or 4-hydroxybenzoate, 4-chlorobenzoate, p-toluenesulphonate, methanesulphonate, ascorbate, acetate, succinate, lactate, glutarate, tricarballylate, hydroxynaphthalene-carboxylate (xinafoate) or oleate salt or solvates thereof.

Many of the above mentioned classes of pharmacologically active compounds may be administered in combination in a separate, sequential or simultaneous way. When administered together the components can be administered as a single pharmaceutical composition such as a fixed combination. Alternatively the components can be administered separately i.e. one after the other. The time interval for separate administration can be anything from sequential administration to administration several hours apart.

The preferred pharmacologically active active glucocortico steroid agents for use in accordance with the present invention includes mometasone (e.g. as furoate), ciclesonide, zoticasone, flumoxonide, fluticasone (e.g. as 17-propionate) and budesonide, and even more preferred is budesonide. The preferred pharmacologically active long-acting β2-agonist is salmeterol (e.g. as xinafoate) and formoterol (e.g. as fumarate dihydrate) and even more preferred is formoterol fumarate dihydrate. The preferred anticholinergic agent is tiotropium bromide.

The preferred combinations include fluticasone propionate/salmeterol xinafoate, ciclesonide/formoterol fumarate dihydrate, mometasone furoate/formoterol fumarate dihydrate, budesonide/formoterol fumarate dihydrate, fluticasone propionate/formoterol fumarate dihydrate and tiotropium bromide/formoterol fumarate dihydrate. The most preferred combination is budesonide/formoterol fumarate dihydrate.

The pharmacologically active ingredients may be administered prophylactically as a preventive treatment or during the course of a medical condition as a treatment of cure.

The composition used in the invention optionally additionally comprises one or more pharmaceutically acceptable additives (e.g. pH or tonicity adjustment), diluents and/or carriers. The composition is preferably in the form of a dry powder for inhalation, wherein the particles of the pharmacologically active ingredients have a mass median diameter of less than 10 µm.

EXAMPLES

Bricanyl® Turbuhaler®, 0.5 mg/dose, a registered trademark from AstraZeneca is a reservoir type of inhaler, where the main assembly (including the dosing mechanism, without mouth piece) was treated in different ways. The metered dose was measured at 60 l/min.

The invention will be illustrated but not limited to the following examples:

Experiment 1

| Treatment | Dose (mg) | Standard deviation (mg) |
|---|---|---|
| Untreated | 0.384 | 0.107 |
| Drying agent/low pressure (40 torr) | 0.545 | 0.069 |

Experiment 2

| | | |
|---|---|---|
| Untreated | 0.439 | 0.088 |
| Drying agent | 0.420 | 0.083 |

Experiment 3

| | | |
|---|---|---|
| Untreated | 0.451 | 0.099 |
| Low pressure (40 torr) | 0.511 | 0.079 |

Experiment 4

Mean values of metered dose (mg) and standard deviations (mg) for 46 analyses of Bricanyl®Turbuhaler® 0.5 mg

| | | |
|---|---|---|
| Untreated | 0.467 | 0.042 |
| Low pressure | 0.534 | 0.029 |

It can be seen that the dose from treated inhalers under reduced pressure will retain the nominal dose of the inhaler and the relative standard deviation will decrease improving the inhaler performance. There is also improvement when e.g. the mouth piece is treated as well. The results further indicate that the process is valid for all kind of compounds/powder formulations and thereby having a more general applicability. The improvement is lasting for a long period of time.

Any complete inhaler including the formulation or just the formulation or parts of the inhaler may also be treated in the same way.

FIG. 1 shows a schematic drawing of the apparatus embodying the present invention where 2=chamber, 4=pump and 6=a device for measuring and controlling the pressure.

FIG. 2 shows Turbuhaler® and its components. Turbuhaler may include a cover 8, an insert holder 10, an insert 12, an indicator holder 14, a dose indicator 16, a body 18, a plug 20, a filling tube 22, scrapers with inhalation channel 24, a dosing unit 26, a pressure plate 28, a spring 30, an operating unit 32, a turning grip 34, spiral channels 36, an inhalation channel 38, one metered dose 40, an air inlet 42, a drug compartment 44, and a dosing unit 46.

The invention claimed is:

1. A method of processing an inhaler component of a dry powder inhaler, the method comprising:
   exposing the inhaler component, while it contains an amount of medicament, to a gas in a chamber at a first predetermined pressure;
   exposing the inhaler component, in the chamber, to gas at a second pressure greater than the first pressure; and
   repeating the exposure of the inhaler component to gas at a pressure no greater than the first predetermined pressure;
   wherein the exposing steps reduce an electrostatic charge of the inhaler component.

2. The method of claim 1, wherein the second pressure is atmospheric pressure.

3. The method of claim 1, wherein the inhaler component is the entire dry powder inhaler.

4. The method of claim 1, comprising twice repeating the exposure of the inhaler component to the gas at the first pressure.

5. The method of claim 1, wherein the gas is air.

6. The method of claim 1, wherein the first pressure is less than 100 mbar.

7. The method of claim 1, wherein the first pressure is less than 50 mbar.

8. The method of claim 1, wherein the first pressure is less than 1 mbar.

9. The method of claim 1, further comprising:
   placing the dry powder inhaler or inhaler component in the chamber;
   closing the chamber;
   reducing the internal pressure of the chamber using a pump; and
   using a measuring device to control the pump so as to reduce the pressure in the chamber to the first pressure,
   wherein the measuring device automatically controls the pump to repeat the exposure of the inhaler component to the gas at the first pressure.

10. The method of claim 1, wherein the medicament is a dry powder formulation, the formulation comprising one or more drugs selected from the group consisting of: mometasone, ciclesonide, zoticasone, flumoxonide, fluticasone, budesonide, salmeterol, formoterol, and tiotropium bromide.

11. The method of claim 1, wherein the medicament is a dry powder formulation, the formulation comprising one or more drug combinations selected from the group consisting of: fluticasone propionate/salmeterol xinafoate, ciclesonide/formoterol fumarate dihydrate, mometasone furoate/formoterol fumarate dihydrate, budesonide/formoterol fumarate dihydrate, fluticasone propionate/formoterol fumarate dehydrate, and tiotropium bromide/formoterol fumarate dihydrate.

12. The method of claim 1, wherein the medicament is a dry powder formulation, the formulation comprising one or more drug combinations selected from the group consisting of budesonide and formoterol fumarate dihydrate.

13. The method of claim 10, wherein the mometasone is furoate.

14. The method of claim 11, wherein the fluticasone is 17-propionate.

15. The method of claim 10, wherein the salmeterol is xinafoate.

16. The method of claim 10, wherein the formoterol is fumarate dehydrate.

17. A method of processing an inhaler component of a dry powder inhaler, the method comprising:
 exposing the inhaler component, in a chamber, to a gas at a first pressure of no more than 100 mbar;
 exposing the inhaler component, in the chamber, to gas at a second pressure greater than the first pressure; and
 repeating the exposure of the inhaler component to gas at a pressure no greater than 100 mbar;
 wherein the exposing steps reduce an electrostatic charge of the inhaler component.

18. The method of claim 17, wherein the second pressure is atmospheric pressure.

19. The method of claim 17, wherein the inhaler component is the entire dry powder inhaler.

20. The method of claim 17, comprising twice repeating the exposure of the inhaler component to the gas at the first pressure.

21. The method of claim 17, wherein the gas is air.

22. The method of claim 17, wherein the first pressure is less than 50 mbar.

23. The method of claim 17, wherein the first pressure is less than 1 mbar.

24. The method of claim 17, further comprising:
 placing the dry powder inhaler or inhaler component in the chamber;
 closing the chamber;
 reducing the internal pressure of the chamber using a pump; and
 using a measuring device to control the pump so as to reduce the pressure in the chamber to the first pressure,
 wherein the measuring device automatically controls the pump to repeat the exposure of the inhaler component to the gas at the first pressure.

25. The method of claim 17, wherein the dry powder inhaler or inhaler component contains a dry powder formulation, the formulation comprising one or more drugs selected from the group consisting of: mometasone, ciclesonide, zoticasone, flumoxonide, fluticasone, budesonide, salmeterol, formoterol, and tiotropium bromide.

26. The method of claim 17, wherein the inhaler component contains a dry powder formulation, the formulation comprising one or more drug combinations selected from the group consisting of: fluticasone propionate/salmeterol xinafoate, ciclesonide/formoterol fumarate dihydrate, mometasone furoate/formoterol fumarate dihydrate, budesonide/formoterol fumarate dihydrate, fluticasone propionate/formoterol fumarate dehydrate, and tiotropium bromide/formoterol fumarate dihydrate.

27. The method of claim 17, wherein the inhaler component contains a dry powder formulation, the formulation comprising one or more drug combinations selected from the group consisting of budesonide and formoterol fumarate dihydrate.

28. The method of claim 25, wherein the mometasone is furoate.

29. The method of claim 26, wherein the fluticasone is 17-propionate.

30. The method of claim 25, wherein the salmeterol is xinafoate.

31. The method of claim 25, wherein the formoterol is fumarate dehydrate.

* * * * *

UNITED STATES PATENT AND TRADEMARK OFFICE
CERTIFICATE OF CORRECTION

PATENT NO. : 8,205,611 B2  
APPLICATION NO. : 12/876493  
DATED : June 26, 2012  
INVENTOR(S) : Magnus Olsson et al.

Page 1 of 1

It is certified that error appears in the above-identified patent and that said Letters Patent is hereby corrected as shown below:

In the Claims

Claim 11, Column 7, Lines 2-3, "dehydrate" should read --dihydrate--.

Claim 16, Column 7, Line 17, "dehydrate" should read --dihydrate--.

Claim 26, Column 8, Line 24, "dehydrate" should read --dihydrate--.

Claim 31, Column 8, Line 38, "dehydrate" should read --dihydrate--.

Signed and Sealed this
Sixteenth Day of February, 2016

Michelle K. Lee
*Director of the United States Patent and Trademark Office*